United States Patent [19]

Musha

[11] Patent Number: 5,601,090
[45] Date of Patent: Feb. 11, 1997

[54] METHOD AND APPARATUS FOR AUTOMATICALLY DETERMINING SOMATIC STATE

[75] Inventor: Toshimitsu Musha, Tokyo, Japan

[73] Assignee: Brain Functions Laboratory, Inc., Kawasaki, Japan

[21] Appl. No.: 274,196

[22] Filed: Jul. 12, 1994

[51] Int. Cl.$^6$ .................................................. A61B 5/04
[52] U.S. Cl. ........................... 128/731; 128/732; 128/733
[58] Field of Search .................................. 128/731, 732, 128/733

[56] References Cited

U.S. PATENT DOCUMENTS

| | | | |
|---|---|---|---|
| 4,140,997 | 2/1979 | Brady | 128/732 |
| 4,462,411 | 7/1984 | Rickards | 128/731 |
| 4,524,774 | 6/1985 | Hildebrandt . | |
| 4,632,122 | 12/1986 | Johansson et al. | 128/731 |
| 4,651,145 | 3/1987 | Sutter | 128/731 |
| 4,683,892 | 8/1987 | Johansson et al. | 128/731 |
| 4,846,190 | 7/1989 | John | 128/731 |
| 4,926,969 | 5/1990 | Wright et al. | 128/731 |
| 4,974,602 | 12/1990 | Abraham-Fuchs et al. | 128/731 |
| 4,977,896 | 12/1990 | Robinson et al. | 128/731 |
| 4,987,903 | 1/1991 | Keppel et al. | 128/731 |
| 5,003,986 | 4/1991 | Finitzo et al. | 128/731 |
| 5,010,891 | 4/1991 | Chamoun | 128/731 |
| 5,230,346 | 7/1993 | Leuchter et al. | 128/731 |
| 5,269,315 | 12/1993 | Leuchter et al. | 128/731 |
| 5,293,427 | 3/1994 | Ueno et al. | 382/1 |
| 5,309,923 | 5/1994 | Leuchter et al. | 128/731 |
| 5,360,971 | 11/1994 | Kaufman et al. | 250/221 |

OTHER PUBLICATIONS

D. Flotzinger, et al., "EEG Classification by Learning Vector Quantization", *Biomedizinischne Technik*, 37, pp. 303–309 (1992).

A. S. Gevins, et al., "Effects of Prolonged Mental Work on Functional Brain Topography", *Electroencephalography and Clinical Neurophysiology*, 76, pp. 339–350 (1990).

B. Kemp, "Cerebral Information Processing Estimated by Unpredictability of the EEG", *Clin. Neurol. & Neurosurg.*, 94, pp. S103–S105 (1992).

B. Klöppel, "Neural Networks As A New Method for EEG Analysis", *Neuropsychobiology*, 29, pp. 33–38 (1994).

B. Klöppel, "Application of Neural Networks for EEG Analysis", *Neuropsychobiology*, 29, pp. 39–46 (1994).

S. Roberts, et al., "New Method of Automated Sleep Quantification", *Med. & Biol. Eng. & Comput.*, 30, pp. 509–517 (1992).

R. A. Veselis, et al., "Use of Neural Network Analysis to Classify Electroencephalographic Patterns Against Depth of Midazolam Sedation in Intensive Care Unit Patients", *J. Clin. Monit.*, 7, pp. 259–267 (1991).

R. A. Veselis, et al., "Analytical Methods To Differentiate Similar Electroencephalographic Spectra: Neural Network and Discriminant Analysis", *J. Clin. Monit.*, 9, pp. 257–267 (1993).

*Primary Examiner*—Angela D. Sykes
*Assistant Examiner*—Stephen Huang
*Attorney, Agent, or Firm*—Fish & Neave; Douglas A. Cardwell

[57] ABSTRACT

An apparatus and a method for automatically determining the present somatic state of a human subject. The characteristic values of the subject (e.g., scalp potential, muscle potential, heart-rate, eye-movement and frequency of eye blinks, or any combination thereof) are detected and output signals corresponding to the detected characteristic values are produced, amplified and digitized. The Fourier transformation is performed on the output signals. A set of state variables for each selected frequency sub-band of a selected frequency band for each of the output signals is determined. Sets of reference weights and sets of reference biases for a neural network from sets of state reference variables corresponding to known somatic states are formed. Each of the sets of state variables, the sets of reference weights and the sets of reference biases are applied to the neural network to determine present somatic state of the subject. The present somatic state of the subject is displayed.

22 Claims, 3 Drawing Sheets

METHOD AND APPARATUS FOR AUTOMATICALLY DETERMINING SOMATIC STATE

BACKGROUND OF THE INVENTION

This invention relates to a method and apparatus for automatically determining somatic state of a human subject, and more particularly to quantifying the somatic state of the human subject to which the apparatus is connected.

There is a continuing demand in the field of human psychology for means whereby the somatic state of subjects can be quantified. A subject's somatic state is the mental state due to such things as the subject's emotions (e.g., joy, anger, happiness, sadness, elation, surprise, disgust or fear), level of mental activity (e.g., as a result of doing mental arithmetic or writing a poem) or motor activity (e.g., moving a hand or foot). Heretofore, psychologists have had to rely on interviews with the subject to elicit information about the subject's somatic state. Questions posed to the subject result in answers that require interpretation based on subjective criteria, and the results achieved by such methods are at best relative.

Somatic states tend to be associated with responses in a number of visceral organs (e.g., the heart, stomach and intestines). However, the particular combination of visceral responses that makes a particular stimulus or state "somatic" is not precisely defined. Similar combinations of visceral responses can be indicative of widely different somatic states. In addition to interviewing the subject, conventionally, psychologists also use electroencephalographic ("EEG") waveforms to interpret the subject's mental state. This too introduces subjective criteria into the analysis because a human expert is required to interpret the EEG waveforms.

Recently, neural networks have come to be used as tools to monitor drug-specific EEG power spectra patterns during the administration of drugs, as shown, for example, by Veselis et al., "Analytical Methods to Differentiate Similar Electrographic Spectra: Neural Network and Discriminant Analysis," 9 *Journal of Clinical Monitoring* 257 (September 1993).

In view of the foregoing, it would be desirable to be able to provide a method and apparatus for automatically determining somatic state, and more particularly to quantifying the somatic state of a human subject to which the apparatus is connected.

SUMMARY OF THE INVENTION

It is an object of this invention to provide a method and apparatus for automatically determining somatic state, and more particularly for quantifying the somatic state of a human subject to which the apparatus is connected. Possible applications of such an apparatus and method might be, for example, determining how much concentration it takes for a subject to do mental arithmetic, quantifying the amount and type of emotion that results from the application of a particular stimulus to the subject, determining emotional stability of a subject over a period of time by exposing the subject to the same stimulus at periodic intervals and measuring his/her response, monitoring the effects of having subjects carry out repetitive tasks in order to develop better methods of reducing repetitive stress disorders, and classifying subjects according to their natural abilities.

These and other objects of the invention are accomplished in accordance with the principles of the invention by providing an apparatus and a method for automatically determining the present somatic state of a subject. Characteristic values of the subject (e.g., scalp potential, muscle potential, heart-rate, eye-movement and frequency of eye blinks, or any combination thereof) are detected and corresponding output signals are produced. The output signals are then amplified and digitized. Fourier transformations are performed on the digitized output signals. A set of state variables is determined for each selected frequency sub-band of a selected frequency band for each of the output signals. Each of the sets of state variables is applied to a trained neural network to determine present somatic state of the subject. The present somatic state of the subject is then displayed. In order to train the neural network, sets of reference weights and sets of reference biases are formed for a neural network using sets of state reference variables corresponding to known somatic states.

BRIEF DESCRIPTION OF THE DRAWINGS

The above and other objects and advantages of the invention will be apparent upon consideration of the following detailed description, taken in conjunction with the accompanying drawings, in which the reference numbers refer to like parts throughout and in which.

DETAILED DESCRIPTION OF THE INVENTION

Figure 1:
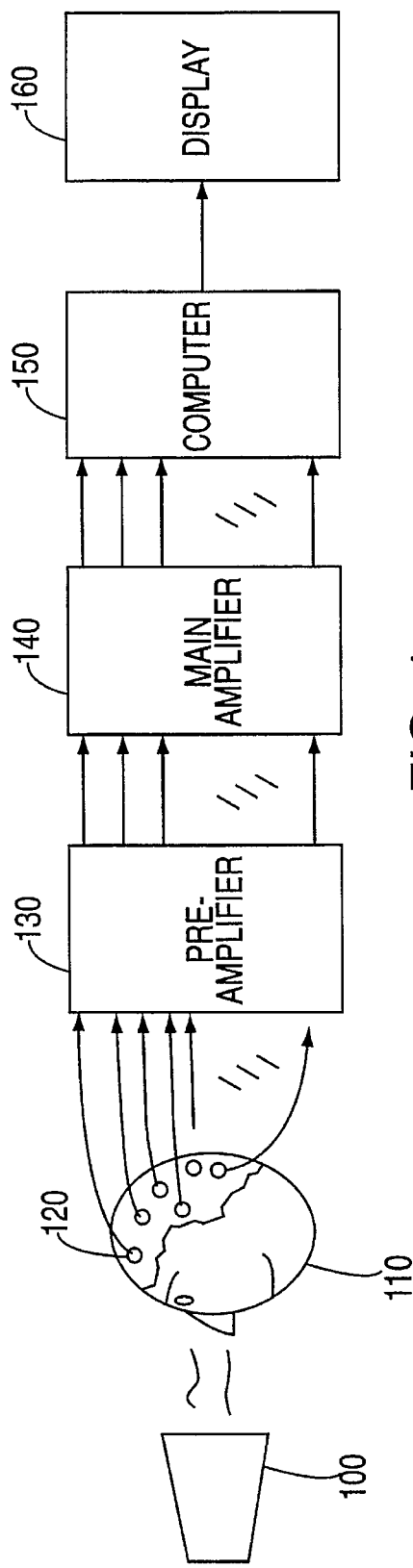
FIG. 1 is a block diagram of a hardware implementation of a preferred embodiment of the apparatus for automatically determining the somatic state of a subject.

The present invention is an apparatus and a method for automatically determining the present somatic state of a subject. Characteristic values of the subject which are indicative of somatic state are detected using sensors. Most typically, brain waves (which can be measured by measuring scalp potential using electrodes) are used as characteristic values. In addition, muscle potential, heart-rate, eye-movement and frequency of eye blinks, or any combination thereof, can be used as characteristic values. The sensors produce output signals corresponding to the detected characteristic values. The output signals are then amplified and digitized. In order to determine the power spectral density of the output signals, Fourier transformations are performed on the digitized output signals. Since some frequency bands are more important sources of somatic state information, only the most important frequency bands are selected. Each selected frequency band is further divided into several sub-bands. A set of state variables is determined for each sub-band of each selected frequency band for each of the output signal power distribution. Each of the sets of state variables is applied to a trained neural network to determine present somatic state of the subject. The present somatic state of the subject is then displayed.

The neural network is trained by forming sets of reference weights and sets of reference biases from sets of state reference variables determined from output signals detected during known somatic states. For example, consider the process of training the neural network to recognize two somatic states, the two emotional somatic states corresponding to happiness and sadness. The subject either imagines a happy thought or is made to be happy. Output signals corresponding to measured characteristic values are produced, amplified and digitized. A power spectral density of the output signal from each sensor is determined by performing the Fourier transformation on the digitized output signals. A set of state reference variables for happiness is obtained from the values of power spectral density from each sub-band of the selected frequency bands. The process is repeated, when the subject is feeling sad, in order to generate a set of state reference variables for sadness.

The purpose of the training phase is to generate a set of reference weights and a set of reference biases that can be used to determine unknown emotional somatic states as either happiness, sadness or neither. A method such as the back-propagation method with supervised learning is often employed. Initially the reference weights and the reference biases are set to random numbers. Then the set of state reference variables for happiness is applied to the neural network and the output of the neural network is compared to the desired output (i.e., happiness) and the values of the reference weights and the reference biases are adjusted accordingly. The process is repeated for sadness. In practice, the process may be repeated for many sets of reference variables corresponding to the emotional somatic states of happiness and sadness in order to further refine the reference weights and reference biases and improve the neural network's ability to recognize happiness and sadness. Ultimately, when the detection error rate has reached an acceptable level, a single set of reference weights and a single set of reference biases that can be used to determine unknown emotional somatic states as either happiness, sadness or neither is generated.

The invention is not limited to distinguishing between two somatic states (the above described emotional states of happiness and sadness). The neural network can be trained to recognize other somatic states (such as the emotional states of joy, anger, happiness, sadness, elation, surprise, disgust or fear, level of mental activity or motor activity).

FIG. 1 is a block diagram of a hardware implementation of a preferred embodiment of the apparatus for automatically determining the somatic state of a subject 110. The stimulus 100, which is applied to the subject 110, may be an externally applied signal such as noise, music or a television picture, or the stimulus 100 can be mental images generated internally by the subject 110 himself/herself. Affixed to the subject 120 is a plurality of sensors 120.

Figure 2:
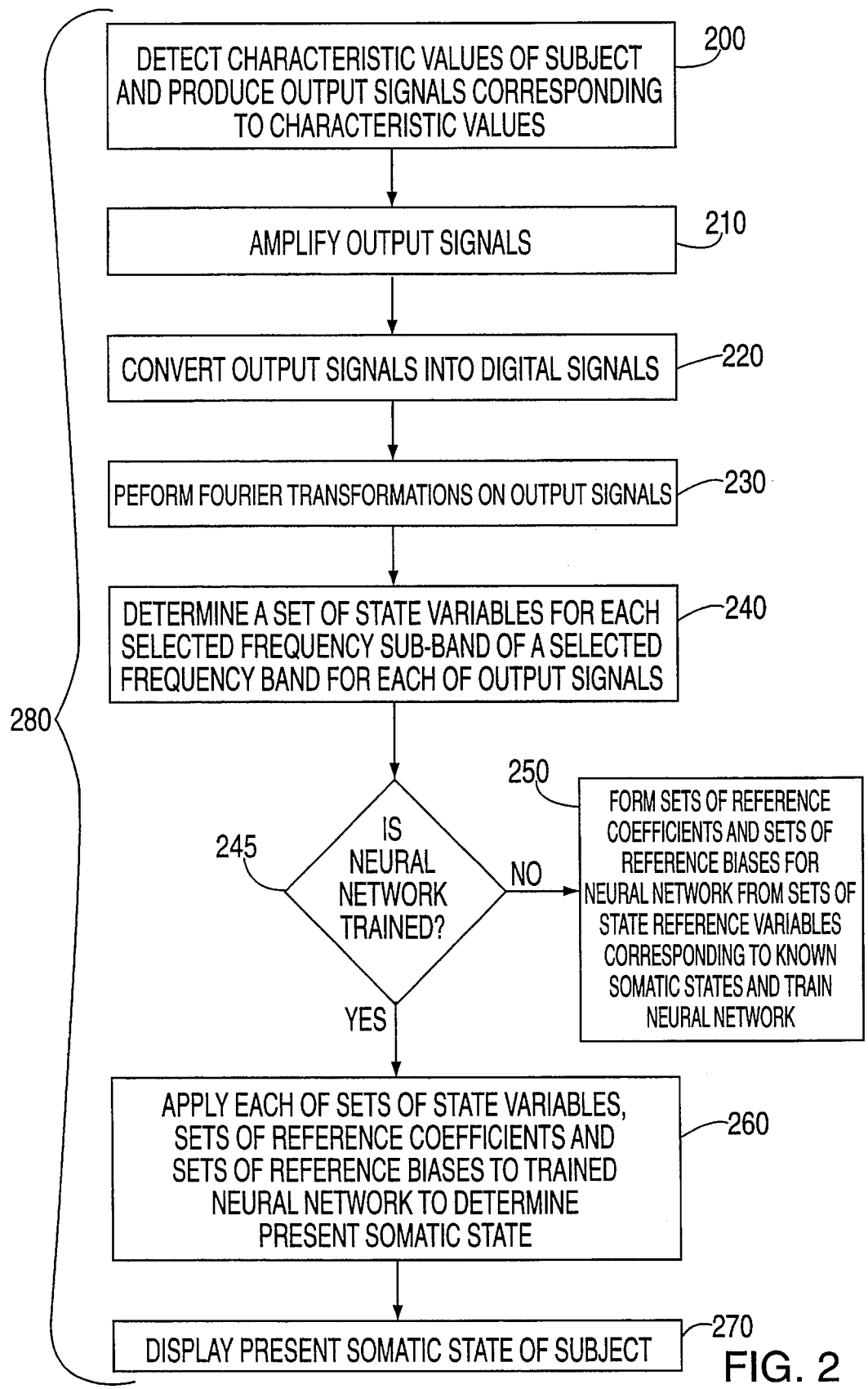
FIG. 2 is a flowchart showing the steps involved in automatically determining the somatic state of a subject.

FIG. 2 shows the steps involved in the process 280 of automatically determining the somatic state of the subject 110. In step 200, the sensors 120 detect characteristic values of the subject 110. Characteristic values refer to those traits, such as scalp potential, muscle potential, heart-rate, eye-movement and frequency of eye blinks of the subject 110, which are indicative of the subject's 110 present somatic state. Indeed, any combination of such characteristic values can be used.

In step 210 of the process 280, the output signals from the sensors 120 are connected to a preamplifier 130 which amplifies the output signals by a predetermined amount. The output signals are then passed through to the main amplifier 140 which amplifies them yet again.

In step 220 of the process 280, the amplified output signals are fed into a computer 150 which digitizes the output signals.

In step 230 of the process 280, the computer 150 performs Fourier transformations on the output signals. The Fourier transform is a well known operation whereby the power spectral density of a signal can be obtained. The Fourier transforms of most signals have both real and imaginary components. Power spectral density is computed by taking the sum of the squares of the real and imaginary components of the Fourier transform for each frequency value of the transformed output signal.

Figure 3:
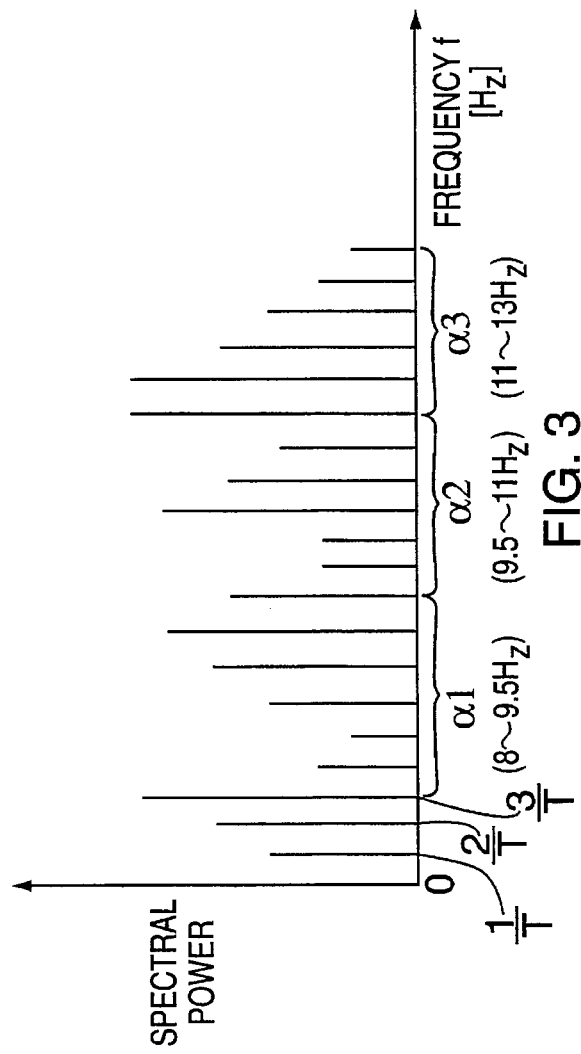
FIG. 3 is an example of a power spectral density that resulted from the Fourier transform of a typical output signal of one of the electrodes attached to the subject, as shown in FIG. 1.

FIG. 3 shows an example of a power spectral density that resulted from the Fourier transform of a typical output signal of one of the sensors 120. In FIG. 3, the duration of the output signal was T seconds and the frequency samples are separated by 1/T Hz. The highest frequency is $\frac{1}{2}\tau$ Hz, where $\tau$ is the sampling rate at which the output signals are digitized in step 220. Thus, there are $(\frac{1}{2}\tau)/(1/T)=T/2\tau$ values for power spectral density.

In step 240, the computer 150 determines a set of state variables for each selected frequency sub-band of a selected frequency band for each of the output signals. During the training phase, in step 250, the set of state variables will be used to train the neural network 280. During normal operation of the neural network, this set of state variables will be applied to a neural network 494 to determine the present somatic state of the subject 110, in step 260.

Brain waves are typically divided into several frequency bands. FIG. 3 shows a power spectral density of only the $\alpha$ band, a band of frequencies between about 8 Hz and about 13 Hz. The $\alpha$ band is an important source of information about somatic state. In addition to the $\alpha$ band, there is the $\delta$ band (from about 1 to about 3 Hz), the $\theta$ band (from about 4 to about 7 Hz), the $\beta$ band (from about 13 Hz to about 30 Hz) and the $\gamma$ band (above about 30 Hz). The following description employs only the $\alpha$ band, but the invention can be applied to any of the other bands. Characteristic values other than brain waves (for example, muscle potential, heart-rate, eye-movement and frequency of eye blinks, or any combination thereof) can also be divided into multiple frequency bands, so the following description applies.

In FIG. 3, the $\alpha$ band is sub-divided into three sub-bands, $\alpha_1$, $\alpha_2$ and $\alpha_3$. Such sub-division can be accomplished by band-pass filtering. In this example the $\alpha_1$ sub-band extends from about 8 to about 9.5 Hz, the $\alpha_2$ sub-band from about 9.5 to about 11 Hz and the $\alpha_3$ sub-band from about 11 to about 13 Hz. For purposes of illustration, assume that there are six sensors 120 attached to the subject 110 for each frequency band. A set of state variables can be created from cross-correlating pairs of the spectral power values of the sensor output signals. The cross-correlation operation for EEG potential $V_j$ measured at the jth electrode and the EEG potential $V_k$ measured at the kth electrode site where j=1, 2, . . . , 6 and k=1,2, . . . ,6 is defined as:

$$\frac{<V_j><V_k>}{(<V_j^2><V_k^2>)^{0.5}}$$

where the <> operator means average over a 5 second interval. Similar expressions are obtained for each of the $\alpha_1$, $\alpha_2$ and $\alpha_3$ sub-bands. There are then $_6C_2=(6\times5)/2=15$ combinations of pairs of sensors 120 for each frequency band and a total of 3×15=45 cross-correlation coefficients which can be used as a set of state variables. Another set of 18 state variables can be generated by adding powers (mean squares) of the electric potential of each of the 6 electrodes for each of the 3 bands. In fact, a set of 63 state variables can be generated by combining the set of 45 state variables with the set of 18 state variables.

Alternatively a set of 306 state variables can be generated from the 51 values of the Fourier transformation from 5 to 15 Hz for each of the 6 sensors 120 where the Fourier transformation is performed every 5 seconds.

In step 250, the computer 150 forms sets of reference weights and sets of reference biases for a neural network. Step 250 is also referred to as the neural network training phase. Each of the sets of reference weights and each of the sets of reference biases is formed from applying to the neural network a set of state reference variables corresponding to a known somatic state.

Figure 4:
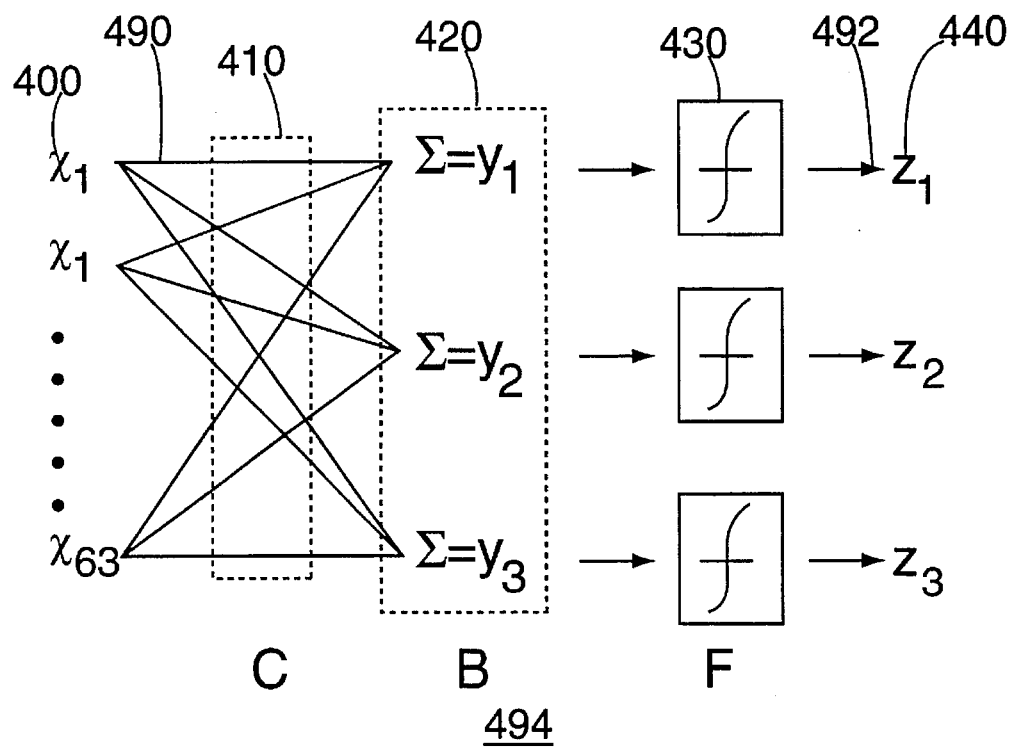
FIG. 4 shows a typical neural network.

FIG. 4 shows a typical neural network 494 composed of two layers, an input layer 490 and an output layer 492. Neural networks with more layers and more neurons can also be used. However, the output layer 492 will always comprise a neuron for each somatic state to be determined. In this case, there are three somatic states to be detected, so output layer 492 has three neurons. The advantages to using neural networks are manifold. In order to build a system which can determine somatic information with high accuracy, the ability of a neural network to use multi-sensor inputs (scalp potential, muscle potential, heart-rate, eye-movement and frequency of eye blinks of the subject, etc) is a big advantage over having a human expert manually review the data. Conventional methods require the human expert to interpret an EEG graph. Indeed, it is possible to train a neural network using incomplete, noisy, redundant or even contradictory data—a big advantage over so-called "expert-systems" which require a complex set of formal rules.

Non-linear transfer functions are sometimes used for in the transfer function stage 430 to compress their inputs (which may have any value between plus and minus infinity) into the range of 0 to 1. A sigmoid transfer function can be used as the non-linear transfer function because it is differentiable. However, since the sigmoid function saturates (produces a value close to one) for most positive inputs, use of the sigmoid function results in a loss of information about the intensity of the somatic state. Therefore in order to preserve maximum information about the intensity of the somatic states, and to avoid the problems associated with a sigmoid function, the function preferably used in the transfer function stage 430 during normal operation is such that for inputs greater than or equal to zero its output is slowly saturating (for example, logarithmic or linear), while for inputs less than zero its output is zero. During the training phase, the function preferably used in the transfer function stage 430 is slowly saturating (for example, logarithmic or linear) for all inputs.

Consider an input layer 490 of neural network 494 composed of 63 inputs 400 $x_1, x_2, \ldots, x_{63}$, a weighting stage 410, a biasing and summing stage 420, a transfer function stage 430 and outputs 440 $z_1, z_2, z_3$. Output layer 492 consists of outputs 440 $z_1, z_2, z_3$. In the training phase, transfer function 430 is a linear transfer function and the weights and biases are adjusted such that outputs corresponding to somatic states 0, 1 and 2 approach $z=[1,0,0]$, $[0,1,0]$ and $[0,0,1]$ respectively. During operation of the trained neural network, the function 430 is such that for inputs greater than or equal to zero its output is linear, while for inputs less than zero its output is zero.

Biases help the neural network 494 to represent relationships between input 400 and output 440 more easily because a neural network layer without a bias has a net output to the following layer of zero when all of its inputs are zero.

At the start of the training phase the weights, represented by the matrix C and the biases, represented by the matrix B are set to random values. When the first set of state reference variables corresponding to a known somatic state is applied to the input 400 and propagated through the neural network 494, the output 440 will likely not indicate the correct somatic state. The output 440 is compared with the desired output 440 and an error is calculated. Training is completed when the difference between the actual output 440 and the desired output 440 is less than a selected value (calculated as the sum of the squares of the difference between the desired and actual output 440). This process is repeated for the sets of state reference variables corresponding to the known somatic states which are to be recognized.

In step 260, the computer 150 applies each of the sets of state variables to the neural network 494 which is formed with the sets of reference weights and the sets of reference biases. Using the neural network 494 to interpret the state variables, the computer 150 is able to determine the present somatic state of the subject 110.

The operation of a trained neural network 494 can be illustrated in reference to FIG. 4 and the following equations. The result of the weighting stage 410 and the biasing and summing stage 420 is expressed as a vector $Y=[y_1, y_2, y_3]$, whereby $$Y = \begin{bmatrix} y_1 \\ y_2 \\ y_3 \end{bmatrix}$$

$$= CX + B$$

$$= \begin{bmatrix} c_1^1 & c_1^2 & c_1^3 & \ldots & c_1^{63} \\ c_2^1 & c_2^2 & c_2^3 & \ldots & c_2^{63} \\ c_3^1 & c_3^2 & c_3^3 & \ldots & c_3^{63} \end{bmatrix} \begin{bmatrix} x_1 \\ x_2 \\ x_3 \\ \vdots \\ x_{63} \end{bmatrix} + \begin{bmatrix} b_1 \\ b_2 \\ b_3 \end{bmatrix}$$

$$= \begin{bmatrix} c_1^1 x_1 + c_1^2 x_2 + c_1^3 x_3 + \ldots c_1^{63} x_{63} + b_1 \\ c_2^1 x_1 + c_2^2 x_2 + c_2^3 x_3 + \ldots c_2^{63} x_{63} + b_2 \\ c_3^1 x_1 + c_3^2 x_2 + c_3^3 x_3 + \ldots c_3^{63} x_{63} + b_3 \end{bmatrix}$$

The vector Y is then operated on by the linear transfer function stage 430 which creates vector Z:

$$Z = \begin{bmatrix} z_1 \\ z_2 \\ z_3 \end{bmatrix}$$

Figure 5:
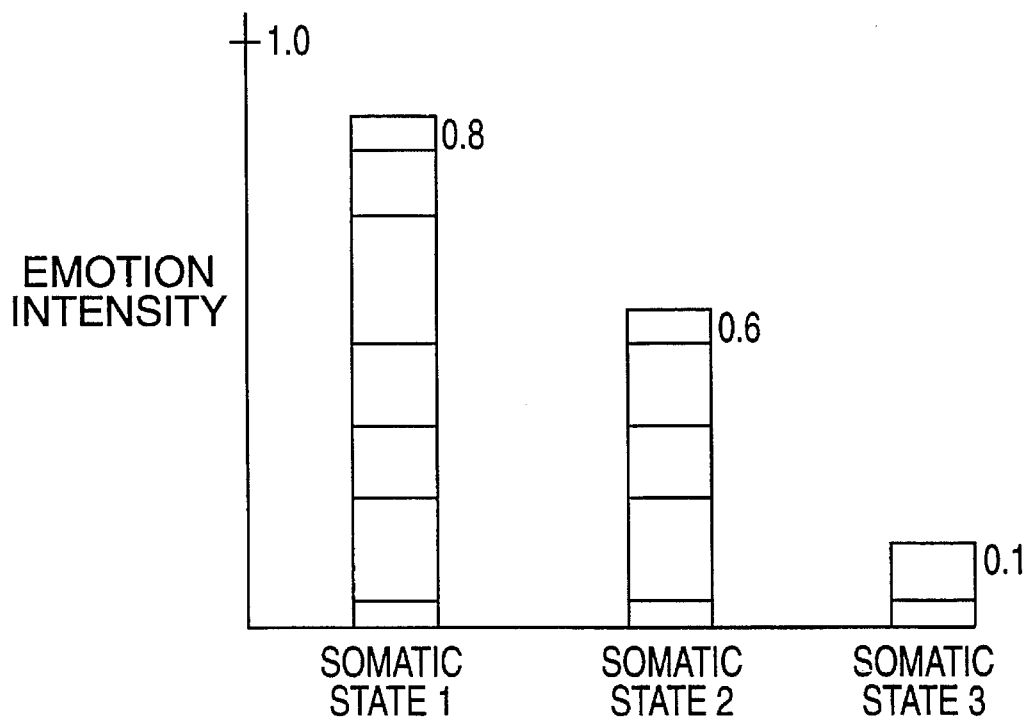
FIG. 5 shows graphically an output vector of the neural network, indicating that the present somatic state of the subject is a weighted combination of the reference somatic states.

In step 270, the computer 150 displays the present somatic state of the subject 110 on a display 60, as shown in FIG. 5.

The neural network 494 of FIG. 4 can recognize combinations of three different reference somatic states, represented by the set of output 440 vectors $Z=\{[1, 0, 0], [0, 1, 0] \text{ and } [0, 0, 1]\}$. The appearance of an output 440 vector, for example $[0.8, 0.6, 0.1]$ as shown graphically in FIG. 5, indicates that the present somatic state of the subject 110 is a weighted combination of the three reference somatic states. Analysis of the somatic state can be performed in nearly real time (for example, every 5 seconds) and monitoring the time change of the somatic state is useful for bio-feedback.

When a sigmoid function is used in the transfer function stage 430 output values tend to cluster, or saturate, about 1 or 0. This is an undesirable effect because information about the relative intensity of a particular somatic state is lost. In particular, a somatic state of strong intensity will always appear as a one.

To avoid the problems associated with a sigmoid function, during normal operation, the function used in the transfer function stage 430 is such that for inputs greater than or equal to zero its output is slowly saturating (for example, logarithmic or linear), while for inputs less than zero its output is zero. During the training phase, the function used in the transfer function stage 430 is slowly saturating (for example, logarithmic or linear) for all inputs.

A neural network of the present invention that has been trained at a particular time to recognize certain somatic states of a given subject will be able to recognize any such somatic state for that subject at any other time. Further, when the reference somatic states are specific enough (for example "joy coming from achievement"), a neural network trained for one subject can be used for any other subject—a universal database.

Consider the application of the present invention to reading the state of mind of a subject who has lost the ability to express his/her wishes verbally or by bodily motion. Using the present invention, such a patient can still communicate with his/her family. Indeed the display 160 could consist of a battery of lamps, each lamp corresponding to a different somatic state. Somatic state intensity is indicated by the brightness of the lamp.

Thus it can be seen that a method and an apparatus for automatically determining the somatic state of a subject, and more particularly for quantifying the somatic state of a human subject, is provided. One skilled in the art will appreciate that the present invention can be practiced by other than the described embodiments, which are presented for purposes of illustration and not of limitation, and the present invention is limited only by the claims which follow.

What is claimed is:

1. Apparatus for automatically determining a present somatic state of a human subject, comprising:

a plurality of sensors which produce output signals for detecting characteristic values of said subject when affixed to a body of said subject;

amplifiers for amplifying said output signals;

a processor for:
  digitizing said output signals,
  performing Fourier transformations on said digitized output signals,
  determining a set of state variables for each of a plurality of selected frequency sub-bands of a selected frequency band for each of said output signals,
  containing sets of reference weights and sets of reference biases for a neural network, wherein each of said sets of reference weights and each of said sets of reference biases is formed from a set of state reference variables corresponding to a known somatic state, and
  applies each of said sets of state variables, and sets of reference weights and said sets of reference biases to said neural network to determine present somatic state of said subject; and a display for displaying the present somatic state of said subject; wherein:

the present somatic state is an emotional state selected from the group consisting of joy, anger, happiness, sadness, elation, surprise, disgust and fear.

2. The apparatus of claim 1 wherein said plurality of sensors detects scalp potential at a plurality of points on scalp of said subject.

3. The apparatus of claim 1 wherein said plurality of sensors detect muscle potential at a plurality of points on body of said subject.

4. The apparatus of claim 1 wherein said plurality of sensors detect heart-rate of said subject.

5. The apparatus of claim 1 wherein said plurality of sensors detect eye movements of said subject.

6. The apparatus of claim 1 wherein said plurality of sensors detect frequency of eye blinks of said subject.

7. The apparatus of claim 1 wherein said set of state variables is created from cross-correlating pairs of spectral power values of the sensor output signals.

8. The apparatus of claim 1 wherein said processor means determines said set of state variables from spectral power of each digitized output signal.

9. The apparatus of any one of claims 1 through 8 wherein said selected frequency band is $\alpha$ band.

10. The apparatus of one of claims 1 through 8 wherein said selected frequency band is $\alpha$ band.

11. The apparatus of any one of claims 1 through 8 wherein said selected frequency band is $\gamma$ band.

12. A method for automatically determining a present somatic state of a human subject, comprising the steps of:

detecting characteristic values of said subject and producing output signals corresponding to said characteristic values;

amplifying said output signals;

digitizing said output signals;

performing Fourier transformations on said digitized output signals;

determining a set of state variables for each of a plurality of selected frequency sub-band of a selected frequency band for each of said output signals;

forming sets of reference weights and sets of reference biases for a neural network from sets of state reference variables corresponding to known somatic states;

applying each of said sets of state variables, said sets of reference weights and said sets of reference biases to said neural network to determine present somatic state of said subject; and displaying the present somatic state of said subject; wherein:

the present somatic state is an emotional state selected from the group consisting of joy, anger, happiness, sadness, elation, surprise, disgust and fear.

13. The method of claim 12 wherein said step of detecting characteristic values comprises detecting scalp potential at a plurality of points on scalp of said subject.

14. The method of claim 12 wherein said step of detecting characteristic values comprises detecting muscle potential at a plurality of points on body of said subject.

15. The method of claim 12 wherein said step of detecting characteristic values comprises detecting heart-rate of said subject.

16. The method of claim 12 wherein said step of detecting characteristic values comprises detecting eye movements of said subject.

17. The method of claim 12 wherein said step of detecting characteristic values comprises detecting frequency of eye blinks of said subject.

18. The method of claim 12 wherein said step of determining said set of state variables comprises cross-correlating pairs of spectral power values of the sensor output signals.

19. The method of claim 12 wherein said step of determining said set of state variables comprises determining spectral power of each digitized output signal.

20. The method of any one of claims 12 through 19 wherein said selected frequency band is α band.

21. The method of any one of claims 12 through 19 wherein said selected frequency band is β band.

22. The method of any one of claims 12 through 19 wherein said selected frequency band is γ band.

* * * * *